United States Patent
Knutsson

(10) Patent No.: US 9,844,647 B2
(45) Date of Patent: Dec. 19, 2017

(54) SPRING CLIP NEEDLE GUARD

(71) Applicant: Vigmed AB, Helsingborg (SE)

(72) Inventor: Per Knutsson, Helsingborg (SE)

(73) Assignee: VIGMED AB (SE)

( * ) Notice: Subject to any disclaimer, the term of this patent is extended or adjusted under 35 U.S.C. 154(b) by 0 days.

(21) Appl. No.: 14/655,889

(22) PCT Filed: Jan. 2, 2014

(86) PCT No.: PCT/SE2014/050001
§ 371 (c)(1),
(2) Date: Jun. 26, 2015

(87) PCT Pub. No.: WO2014/107133
PCT Pub. Date: Jul. 10, 2014

(65) Prior Publication Data
US 2015/0335864 A1     Nov. 26, 2015

(30) Foreign Application Priority Data

Jan. 3, 2013 (SE) ...................................... 1350003

(51) Int. Cl.
*A61M 25/06* (2006.01)
*A61M 5/32* (2006.01)
(52) U.S. Cl.
CPC ...... *A61M 25/0618* (2013.01); *A61M 5/3257* (2013.01); *A61M 5/3273* (2013.01);
(Continued)
(58) Field of Classification Search
CPC .......... A61M 25/0606; A61M 25/0618; A61M 25/0612
(Continued)

(56) References Cited

U.S. PATENT DOCUMENTS

2002/0103463 A1   8/2002   Luther et al.
2003/0060774 A1*   3/2003   Woehr ................ A61M 5/3273
                                                                       604/192
(Continued)

FOREIGN PATENT DOCUMENTS

AU        200142070 A1    2/2002
AU        20092336123      11/2009
WO      WO-2014107133 A1    7/2014

OTHER PUBLICATIONS

Chinese Office Action 201480003954.6, dated Feb. 27, 2017.

*Primary Examiner* — Kevin C Sirmons
*Assistant Examiner* — Amber Stiles
(74) *Attorney, Agent, or Firm* — Fishman Stewart PLLC

(57) ABSTRACT

A spring clip needle tip shielding device for arrangement in a catheter hub of an intravenous catheter assembly is provided. The spring clip needle tip shielding device comprises a base plate with a hole extending therethrough and at least one resilient arm extending at an attachment point at said base plate. The at least one resilient arm has a resting state, from which it may be urged to yield free passage through said hole in an axial direction of said base plate in a tension state, said at least one resilient arm being adapted for clamping a needle tip of a needle extending through said hole when said resilient arm is in said resting state. Any straight imaginary line extending longitudinally through said hole in the axial direction of said base plate coincides with said at least one resilient arm when said resilient arm is in said resting state of said body. The spring clip needle tip shielding device is of a rigid material, and at least a part thereof is coated with a solid lubricant. A catheter assembly including such shielding device is also provided.

12 Claims, 2 Drawing Sheets

(52) U.S. Cl.
CPC . *A61M 25/0606* (2013.01); *A61M 2205/0211* (2013.01); *A61M 2205/0222* (2013.01); *A61M 2205/0238* (2013.01)

(58) Field of Classification Search
USPC ............ 604/164.01, 164.06, 164.07, 164.08, 604/165.01, 263, 272
See application file for complete search history.

(56) References Cited

U.S. PATENT DOCUMENTS

| | | | |
|---|---|---|---|
| 2007/0098984 A1* | 5/2007 | Peterson, II | D01F 8/04 428/375 |
| 2007/0110733 A1* | 5/2007 | Lum | A61K 47/48776 424/93.21 |
| 2007/0232502 A1* | 10/2007 | Tsutsui | C08J 9/40 508/104 |
| 2009/0182280 A1* | 7/2009 | Glowacki | A61M 25/0625 604/164.08 |
| 2011/0060294 A1* | 3/2011 | Baid | A61M 25/0618 604/263 |
| 2011/0160671 A1 | 6/2011 | Tanabe et al. | |
| 2012/0220956 A1 | 8/2012 | Kuracina et al. | |

\* cited by examiner

SPRING CLIP NEEDLE GUARD

CROSS-REFERENCE TO RELATED APPLICATIONS

This application is a U.S. National phase based on PCT/SE2014/050001, filed on Jan. 2, 2014 entitled "SPRING TIP NEEDLE GUARD" which is based on Swedish Patent Application No. 1350003-8, filed on Jan. 3, 2013, each of which is hereby incorporated by reference in its entirely.

TECHNICAL FIELD

The present disclosure relates to a spring clip needle guard, and a catheter instrument comprising such a spring clip needle guard, for the automatic safety shielding of a needle after its employment for introduction of a catheter tube.

BACKGROUND

The clinical utilization of a pointed hollow needle mounted inside a flexible catheter tube may be utilized in the medical art for the introduction of a catheter. In such a medical instrument, the catheter tube is positioned tightly around the needle in such a way as to allow the needle to slide and telescope along the length of the catheter tube. Before use, the tip of the needle is protruding slightly through the opening of the catheter tube to allow facile penetration through the skin. Upon puncturing of the skin and introduction of the needle, the distal end of the catheter tube is simultaneously brought into place inside the desired target body cavity of the patient, such as the inside of a blood vessel, for example a vein. The needle has then done its duty in assisting the introduction of the catheter and is withdrawn by being pulled backwards through the catheter. Upon release of the needle, the catheter is set in its intended working mode extending over a lengthier period of time and including, for example, periodical administration or infusion of fluids or medications in liquid form, the collection of blood samples and the like.

An unprotected released needle constitutes, however, a serious health hazard due to the fact that it may be contaminated with e.g. infectious agents originating from the patient's blood or other body fluids, in combination with the needle tip's inherent ability to easily penetrate skin. Hence, the medical personnel who are handling the released needle may acquire the corresponding disease, e.g. HIV or hepatitis, if by accident contacting it with their skin. In order to circumvent or alleviate the health hazards associated with such a released needle amongst other things, there has been much effort devoted to the development of various kinds of needle tip protectors with a special focus on automatic variants of a type which may be referred to as being "foolproof".

EP 1 003 588. discloses a safety IV catheter comprising a resilient spring clip normally positioned in the catheter hub. The needle of the safety IV catheter passes through a hole in the spring clip which allows axial movement of the needle. When the needle is in the forward position, i.e. when the safety IV catheter is ready for use, the presence of the needle forces parts of the spring clip into a position where these parts locks to the inside of the catheter hub, whereby movement of the spring clip relative the catheter hub is prevented. As the needle is withdrawn to a point where the tip passes these parts, the spring clip snaps into a position in which it is blocking access to the to the tip of the needle. Simultaneously, the part of the spring clip that previously locked to the inside of the catheter hub snap out of this position, whereby movement of the spring clip relative the catheter hub may occur. As the needle is further withdrawn, means are provided, e.g. a slot or a crimp on the needle, to lock the spring clip to the needle, whereby the spring clip is ejected from the catheter hub together with, and positioned on, the needle.

For various reasons, including e.g. practical, economical and technical reasons, the above described spring clips, and similar marketed variants, are today made of metal and catheter hubs of a plastic material. Disadvantages of the combination of these materials in this application include the release of e.g. microscopic plastic chips and metallic particles by the scraping of the metal spring clip against the inside of the plastic catheter hub when the former is ejected from the latter upon withdrawal of the needle. These chips and particles may easily be flushed into the bloodstream of a patient upon normal use of the corresponding catheter, and thus represent a serious health hazard to the same. This is especially true when the spring clip needs to pass beyond a bulge or something similar within the cavity of the catheter hub, onto which the metal spring clip should be brought into retained position until being released when the needle tip passes the distal part of the metal spring clip. Another disadvantage of the spring clip of this and similar safety IV catheters is the scraping vibration generated as the needle slides through and on the spring clip as it is withdrawn. This scraping vibration, which is due to metal sliding over metal and which can be clearly heard and felt, is highly uncomfortable and worrisome to the patient, who already is in an uncomfortable and exposed situation and may be very anxious.

Hence, an improved device for automatic shielding of the needle tip of a needle after its employment for introduction of a catheter tube is desired.

BRIEF DESCRIPTION OF THE DRAWINGS

These and other aspects, features and advantages of which the disclosure is capable of will be apparent and elucidated from the following description of embodiments of the present disclosure, reference being made to the accompanying drawings, in which.

DESCRIPTION OF EMBODIMENTS

Accordingly, the present disclosure preferably seeks to mitigate, alleviate or eliminate one or more of the above-identified deficiencies in the art and disadvantages singly or in any combination and solves at least the above mentioned problems by providing a spring clip needle tip shielding device for arrangement in a catheter hub of an intravenous catheter assembly, said spring clip needle tip shielding device comprising: a base plate with a hole extending therethrough; at least one resilient arm extending at an attachment point at said base plate; wherein said at least one resilient arm has a resting state, from which it may be urged to yield free passage through said hole in an axial direction of said base plate in a tension state, said at least one resilient arm being adapted for clamping a needle tip of a needle extending through said hole when said resilient arm is in said resting state; and wherein any straight imaginary line extending longitudinally through said hole in the axial direction of said base plate coincides with said at least one resilient arm when said resilient arm is in said resting state; and wherein said spring clip needle tip shielding device is of a rigid material, and at least a part thereof is coated with a solid lubricant.

For the same reasons a catheter instrument is provided, said catheter instrument comprising a spring clip needle tip shielding device according to above, a catheter unit and a needle unit; wherein said catheter unit comprises a catheter hub and a catheter extending distally from the catheter hub, said catheter having a lumen being in flow communication with an interior cavity of the catheter hub; wherein said needle unit comprises a needle hub and a needle with a needle shaft and a needle tip extending distally from the needle hub; said needle hub being connected to the proximal end of the catheter hub and said needle shaft being arranged in the lumen of the catheter, in a ready position of said catheter instrument, and said spring clip needle tip shielding device being arranged inside the interior cavity of the catheter hub, and said needle being arranged through said hole with the resilient arm being urged into its tension state by said needle shaft.

Figure 1:
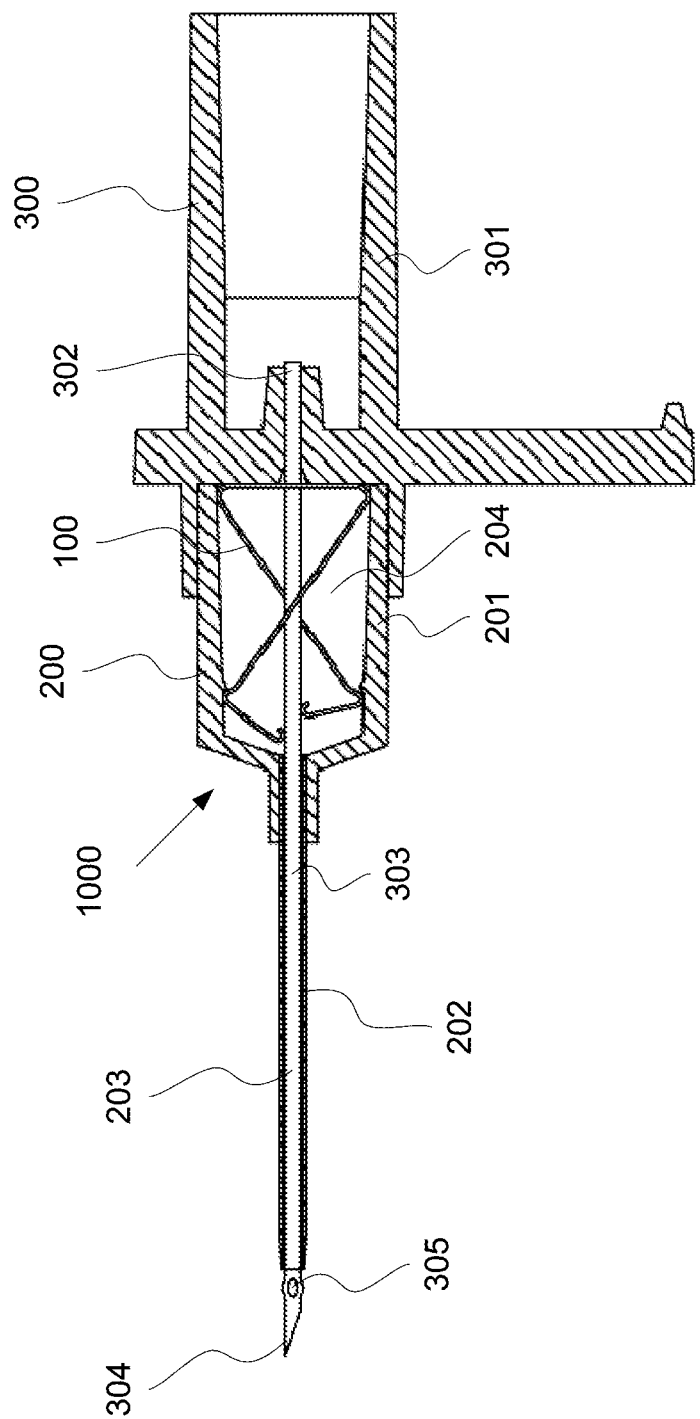
FIG. 1 is a cross sectional view of a catheter instrument according to one embodiment of the present disclosure.
Figure 2:
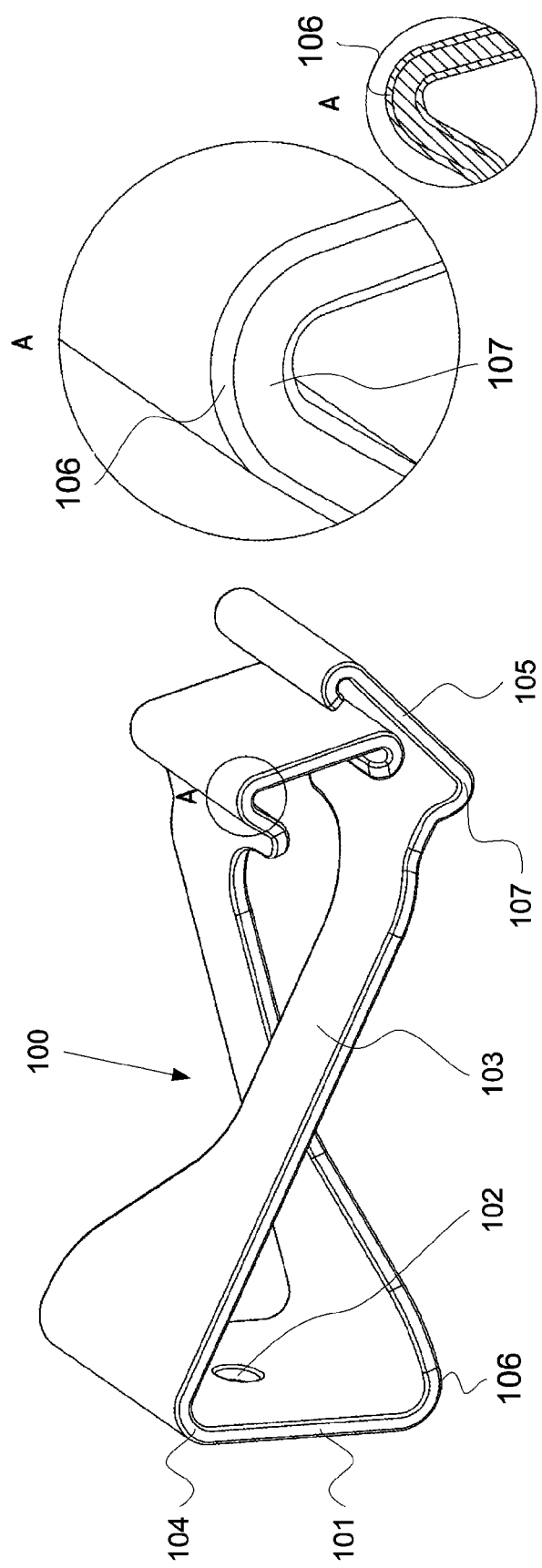
FIG. 2 is a perspective view of a spring clip needle tip shielding device according to one embodiment of the present disclosure.

Embodiments of the present disclosure will be described in more detail below with reference to the accompanying FIGS. 1 and 2 in order for those skilled in the art to be able to carry out the disclosure.

The safety IV catheter instrument 1000 includes a spring clip needle tip shielding device 100, a catheter unit 200 and a needle unit 300.

The catheter unit 200 comprises a catheter hub 201 and a catheter 202 extending distally from the catheter hub 201. The catheter 202 is hollow and tubular, and configured to house a needle stem therein. The catheter 202 is made of a suitable polymeric material. The catheter hub 201 is also made of a suitable polymeric material, such as polypropylene or polyethylene, which are cheap plastic materials with good injection molding properties. The hollow and tubular configuration of the catheter 202 provides a lumen 203 that is in flow communication with an interior cavity 204 of the catheter hub 201. The interior cavity 204 is positioned in the proximal end of the catheter hub 201, and the proximal opening into the interior cavity 204 may end in a luer fitting, such as a luer lock or luer slip, adapted to receive a tubing set that administers intravenous fluid into the patient. The catheter unit 200 thus comprises a catheter hub 201 and a catheter 202 extending distally from the catheter hub 201, said catheter 202 having a lumen 203 being in flow communication with an interior cavity 204 of the catheter hub 201.

The catheter 202 is secured within an axial passageway in distal hub section by means of a sleeve received within passageway, which engages the proximal end of the catheter. This passageway communicates at its proximal end with interior cavity 204, which also acts as a flash chamber, formed in catheter hub 201. The distal end of the catheter 202 may be tapered, to facilitate introduction into the vein of the patient.

The needle unit 300 of the catheter instrument 1000 comprises a needle hub 301. A needle 302 extends distally from the needle hub 301. The needle hub 301 may have an axial opening for receiving the proximal end zone of the needle 302. The needle 302 comprises a needle shaft 303 and a needle tip 304, said needle tip 304 forming the distal end point of the needle unit 300. The needle hub 301 may be hollow and may include a flash chamber at its proximal end.

The needle 302 is received within a hollow tubular catheter 202, the proximal end of which is concentrically affixed within the distal end of a catheter hub 201. At the distal end zone of the needle shaft 303, the needle 302 is provided with a bulge 305. The needle unit 300 thus comprises a needle hub 301 and a needle 302 with a needle shaft 303 and a needle tip 304 extending distally from the needle hub 301.

In the ready position of the catheter instrument 1000, the distal end of the needle hub 301 is snugly received in the proximal end of the interior cavity 204 of the catheter hub 201, such that the needle 302 extends through the cavity 204, the passageway and distally beyond the catheter hub 201 and catheter 202 so that the needle tip 304 extends beyond a the distal end of the catheter 202. Thus, the needle hub 301 is connected to the proximal end of the catheter hub 201 and said needle shaft 303 is arranged in the lumen 203 of the catheter 202, in a ready position of said catheter instrument 1000. The needle hub 301 may be connected to the proximal end of the catheter hub 201 and said needle shaft 303 being arranged in the lumen 203 of the catheter 202, in a ready position of said catheter instrument 1000.

In use, the distal tip 304 of the needle 302 and the catheter 202 are inserted into a patient's vein. Thereafter, the health care practitioner manually places the catheter 202 further into the vein and then withdraws the needle by grasping and moving by hand the proximal end of the needle unit 300. The luer of the catheter hub 200, in the proximal end of the cavity 204, is then fitted with a source of the fluid that is to be administered into the patient's vein.

The spring clip needle tip shielding device 100 is arranged inside the interior cavity 204 of the catheter hub 201. The spring clip needle tip shielding device 100 comprises a base plate 101. The base plate 101 is provided with a hole 102, extending therethrough, i.e. from the proximal side of the base plate 101 to the distal side of the base plate. Preferably, the hole 102 is arranged centrally on the base plate 101, such that arrangement of needle 302 through said hole 102 is facilitated while the needle 302 is arranged in accordance with the ready position of the catheter instrument 1000.

A first resilient arm 103 is extending distally from an attachment point 104 at said base plate 101. Preferably, due to manufacturing reasons, the attachment point 104 is located at the periphery of the base plate 101. The resilient arm 103 has a resting state, from which it may be urged to yield free passage for the needle 302 through said hole 102 in an axial direction of said base plate 101 in a tension state. The resilient arm 103 is in its tension state when the catheter instrument 1000 is in its ready position. The resilient arm 103 is adapted for clamping a needle tip 304 of a needle 302 extending through the hole 102 when the resilient arm 103 is in said resting state. For this reason, a straight imaginary line extending longitudinally through said hole 102 in the axial direction of said base plate 101 coincides with said at least one resilient arm 103 when said resilient arm 103 is in said resting state. This may be facilitated by providing the resilient arm 103 with a distal hook element 105, at the distal end of the resilient arm 103. The spring clip needle tip shielding device 100 may thus be arranged inside the interior cavity 204 of the catheter hub 201, and said needle being arranged through said hole 102 with the resilient arm 103 being urged into its tension state by said needle shaft 303.

The spring clip needle tip shielding device 100 is manufactured in a rigid material, with good flexibility. Such a material is for example a metal, such as stainless steel. The resilient arm 103 is then dimensioned such that it may be flexed into its tension state when the catheter instrument 1000 is in its ready position. The rigid material of the spring clip needle tip shielding device 100, such as metal, such as stainless steel, risk to damage the walls of the interior cavity 204 of the polymeric catheter hub 201 during arrangement of the spring clip needle tip shielding device 100 in the interior cavity into the ready position of the catheter instrument 1000. Also, the metal of the spring clip needle tip shielding device 100 generates unpleasant sounds when gliding on the needle 302. For this reason the spring clip needle tip shielding device 100 is coated, fully or partly, with a solid lubricant 106. The coating 106 may for example be provided on the surfaces that will come in contact with the walls of the interior cavity 204 and/or the needle 302, to mitigate one or all of the problems associated with metal spring clip needle tip shielding devices. For manufacturing reasons, the entire spring clip needle tip shielding device 100 may be coated. Suitable solid lubricants 106 may for example be selected among polymers, graphite, molybdenum disulfide, hexagonal boron nitride, tungsten disulfide, a ceramic, or combinations thereof. A suitable polymer is a flouropolymer, and a suitable flouroploymer is polytetrafluoroethylene. These materials may be useful when considering the preservation of good release and frictional properties also after long lasting storing, while also providing for excellent properties with regard to adhesion to the metal base, such that release of solid lubricant 106 from the spring clip needle tip shielding device 100 when using the catheter instrument 1000, such that solid lubricant may risk to enter the blood stream of the patient, may be decreased.

The resilient arm 103 of said spring clip needle tip shielding device 100 may comprise a central portion 107 being urged by said needle shaft 303 into retaining contact with an interior wall of said catheter hub 201. In this may the interaction between the catheter unit 200 and the spring clip shielding device 100 may be broken once the needle 302 has been displaced proximally into a position where the distal end of the resilient arm 103 falls down in front of the needle tip 304, which in turn makes the central portion 106 to be displaced centrally. When the central portion 107 of the resilient arm 103 is displaced centrally, the spring clip needle tip shielding device 100 looses its contact with the interior wall of said catheter hub 201. Alternatively, the spring clip shielding device 100 is held in place in the catheter hub 201 through friction between the base plate 102 and the interior wall of the catheter hub 201.

In one embodiment the central portion 107 of the resilient arm 103 comprises a traverse segment, traversing the central axis of the hole 102, and thus also the central longitudinal axis of the catheter unit 200. The traverse segment then extends from a lateral end of the base plate 102, across the path of the needle 302. The traverse segment may then be provided with a through hole or cut-out, to enable the needle 302 to pass distally beyond the traverse segment. In this way, the spring clip needle tip shielding device 100 may be stabilized, since the interaction between the needle shaft 303 and the base plate 102 is quite low in needle tip shielding devices made of a bent metal sheet.

After the distal tip 304 of the needle 302 and the catheter 202 have been inserted into a patient's vein, the needle unit 300 is displaced proximally in relation to the catheter unit 200 and the spring clip needle tip shielding device 100. The spring clip needle tip shielding device 100 is retained in the catheter hub 201 of the catheter unit 200 through interaction between the base plate 102 or the central portion 107 of the resilient arm 103, in accordance with above. When the needle unit 300 is displaced proximally in relation to the catheter unit 200 and the spring clip needle tip shielding device 100, also the needle 302 is displaced proximally in relation to these two. Once the needle tip 304 passes proximally beyond the distal end of the resilient arm 103, such as the hook element 105, the distal end of the resilient arm 103 snaps in front of the needle tip 304. The bulge 305 on the needle shaft 303 then hits the base plate 102, since the bulge 305 has been dimensioned with a somewhat larger diameter than the through hole of the base plate 102. Also, the bulge 305 has been positioned on the needle shaft at a distance from the needle tip 304 largely corresponding to the distance between the base plate 102 and the distal end of the resilient arm 103, such that the spring clip needle tip shielding device 100 may be secured at the distal end of the needle 302 once the needle tip 304 has been displaced proximally beyond the distal end, such as the hook element 105, of the spring clip needle tip shielding device 100. In this position, the spring clip needle tip shielding device 100 is released from the catheter unit 200 through overcoming the frictional force between the base plate 102 and the interior wall of the catheter hub 201 or by the central displacement of the central portion 107 of the resilient arm 103, in accordance with above.

The spring clip needle tip shielding device 100 may be provided with more than one resilient arm 103. This additional resilient arm may also traverse the central axis of the catheter unit 200, and may thus also be provided with a through hole or a cut-out for letting the needle 301 pass therethrough. An additional resilient arm may further stabilize the positioning of the spring clip needle tip shielding device 100 on the needle shaft 300. Also the second resilient arm may be provided with a distal hook element for central displacement once the needle tip 304 have passed proximally beyond the distal end of the first and second resilient arms 103.

Although the present disclosure has been described above with reference to specific embodiments, it is not intended to be limited to the specific form set forth herein. Rather, the disclosure is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A spring clip needle tip shielding device for arrangement in a catheter hub of an intravenous catheter assembly, said spring clip needle tip shielding device comprising:
   a base plate with a hole extending therethrough;
   at least one resilient arm extending at an attachment point at said base plate; and
   a solid coating disposed on a contact region of the base plate or the at least one resilient arm, the solid coating on the contact region being configured to contact an inner surface of the catheter hub;
   wherein said at least one resilient arm has a resting state configured to be urged to yield free passage through said hole in an axial direction of said base plate in a tension state, said at least one resilient arm being adapted for clamping a needle tip of a needle extending through said hole when said resilient arm is in said resting state; and wherein any straight imaginary line extending longitudinally through said hole in the axial direction of said base plate coincides with said at least one resilient arm when said resilient arm is in said resting state; and wherein said spring clip needle tip shielding device is of a rigid material.

2. The spring clip needle tip shielding device according to claim 1, wherein the rigid material is metal.

3. The spring clip needle tip shielding device according to claim 2, wherein the metal of said spring clip needle tip shielding device includes stainless steel that is flexed into a tension state when the intravenous catheter assembly is in a ready position.

4. The spring clip needle tip shielding device according to claim 1, wherein said solid coating of the contact region is selected from the group consisting of polymer, graphite, molybdenum disulfide, hexagonal boron nitride, tungsten disulfide, a ceramic, or combinations thereof.

5. The spring clip needle tip shielding device according to claim 4, wherein said polymer is a fluoropolymer.

6. The spring clip needle tip shielding device according to claim 5, wherein said fluoropolymer is polytetrafluoroethylene.

7. A catheter instrument comprising:
a spring clip needle tip shielding device including a base plate with a hole and at least one resilient arm;
a catheter unit; and
a needle unit;
wherein said catheter unit comprises a catheter hub and a catheter extending distally from the catheter hub, said catheter having a lumen being in flow communication with an interior cavity of the catheter hub;

wherein said needle unit comprises a needle hub and a needle with a needle shaft and a needle tip extending distally from the needle hub;

said needle hub being connected to the proximal end of the catheter hub and said needle shaft being arranged in the lumen of the catheter, in a ready position of said catheter instrument, and said spring clip needle tip shielding device being arranged inside the interior cavity of the catheter hub, and said needle being arranged through said hole with the resilient arms being urged into its tension state by said needle shaft; and said spring clip needle tip shielding device including a solid coating disposed on a contact region of the base plate or the at least one resilient arm, the solid coating on the contact region being configured to contact an inner surface of the catheter hub.

8. The catheter instrument according to claim 7, wherein the solid coating of said spring clip needle tip shielding device is urged by said needle shaft into retaining contact with the inner surface of said catheter hub.

9. The spring clip needle tip shielding device according to claim 1, wherein the solid coating is configured to selectively release from to the inner surface of the catheter hub in response to being centrally displaced.

10. The catheter instrument according to claim 7, wherein the solid coating is configured to selectively release from the inner surface of the catheter hub in response to being centrally displaced.

11. The spring clip needle tip shielding device according to claim 1, wherein the solid coating is disposed on bent portion of the at least one resilient arm.

12. The catheter instrument according to claim 7, wherein the solid coating is disposed on a bent portion of the at least one resilient arm.

* * * * *